(12) United States Patent
Bouttens et al.

(10) Patent No.: US 6,953,478 B2
(45) Date of Patent: Oct. 11, 2005

(54) SHOULDER PROSTHESIS ASSEMBLY

(75) Inventors: Denis Bouttens, Le Touquet (FR); Michel De Buttet, Croix (FR); Didier Capon, Sautron (FR); Michel Colmar, Saint Brieuc (FR); Cécile Nerot, Reims (FR); Philippe Valenti, Champigny sur Marne (FR); Hassan Wahab, Angers (FR)

(73) Assignee: Depuy France, Saint-Priest (FR)

( * ) Notice: Subject to any disclaimer, the term of this patent is extended or adjusted under 35 U.S.C. 154(b) by 0 days.

(21) Appl. No.: 10/168,802

(22) PCT Filed: Dec. 14, 2000

(86) PCT No.: PCT/FR00/03539

§ 371 (c)(1),
(2), (4) Date: Oct. 30, 2002

(87) PCT Pub. No.: WO01/47442

PCT Pub. Date: Jul. 5, 2001

(65) Prior Publication Data
US 2003/0114933 A1 Jun. 19, 2003

(30) Foreign Application Priority Data
Dec. 23, 1999 (FR) .................................. 99 16420

(51) Int. Cl.⁷ ................................................ A61F 2/40

(52) U.S. Cl. ................. 623/19.11; 623/19.13; 623/23.11; 623/23.42; 623/22.42

(58) Field of Search .................. 623/19.11–19.14, 623/22.11, 18.11, 23.11–23.14; 433/174; 411/427, 436, 437, 386

(56) References Cited

U.S. PATENT DOCUMENTS

| 3,815,157 | A | * | 6/1974 | Skorecki et al. | ......... 623/19.12 |
| 3,869,730 | A | * | 3/1975 | Skobel | .................... 623/19.12 |
| 3,916,451 | A | * | 11/1975 | Buechel et al. | ............ 623/23.4 |

(Continued)

FOREIGN PATENT DOCUMENTS

EP  0 058 744  9/1982

(Continued)

*Primary Examiner*—Bruce Snow
*Assistant Examiner*—Cheryl Miller
(74) *Attorney, Agent, or Firm*—Young & Thompson

(57) ABSTRACT

The invention concerns a shoulder prosthesis assembly comprising a meta-glenoid element (7) formed by a plate (13) provided with a central tubular block (14) an anchoring members in the glenoid cavity (3), and a glenoid sphere (9) designed to top the metaglenoid element and provided with an axial screw (35) screwed into said pin; the glenoid sphere has an articulated surface (11) designed to co-operate with a cup of an associated humeral prosthesis (2); said assembly comprises means (16, 45, 46; 51, 50, 49) guiding the glenoid sphere adapted to facilitate its being fixed on the meta-glenoid element; said means comprise a pin (46) adapted to be slotted into the tubular block (14) and into an axial passage of the screw (35); the glenoid sphere (9) is thus guided by being slid on the pin (46) until the screw (35) is inserted precisely into the axis of the tubular block (14), wherein it can be screwed without any risk of damaging the thread on the screw and the internal thread of the block. Advantageously, the free end (48) of the screw (35) can likewise be bevelled to facilitate its being inserted in the block (14) without damaging the threads. The inventive arrangement is particular useful considering the difficulties encountered by the surgeon for correctly positioning the glenoid sphere (9) relative to the meta-glenoid element (7) owing to lack of visibility.

11 Claims, 4 Drawing Sheets

U.S. PATENT DOCUMENTS

| | | | | |
|---|---|---|---|---|
| 3,978,528 A | * | 9/1976 | Crep | 623/19.12 |
| 4,040,131 A | * | 8/1977 | Gristina | 623/19.12 |
| 4,693,723 A | * | 9/1987 | Gabard | 623/19.12 |
| 4,964,865 A | * | 10/1990 | Burkhead et al. | 623/19.11 |
| 5,462,563 A | * | 10/1995 | Shearer et al. | 623/20.11 |
| 5,725,595 A | | 3/1998 | Gustilo | |
| 6,228,120 B1 | * | 5/2001 | Leonard et al. | 623/19.12 |
| 6,283,999 B1 | * | 9/2001 | Rockwood, Jr. | 623/19.12 |
| 6,474,918 B1 | * | 11/2002 | Kelch | 411/180 |
| 2003/0149485 A1 | * | 8/2003 | Tornier | |
| 2003/0158605 A1 | * | 8/2003 | Tornier | |

FOREIGN PATENT DOCUMENTS

| | | | | |
|---|---|---|---|---|
| EP | 0 243 298 | | 10/1987 | |
| EP | 0 379 785 | | 8/1990 | |
| EP | 0 581 667 | | 2/1994 | |
| EP | 0 910 999 | | 4/1999 | |
| FR | 2 652 498 | | 4/1991 | |
| FR | 2704747 | * | 6/1993 | A61F 2/40 |
| FR | 2 704 747 | | 11/1994 | |
| FR | 2 737 107 | | 1/1997 | |

\* cited by examiner

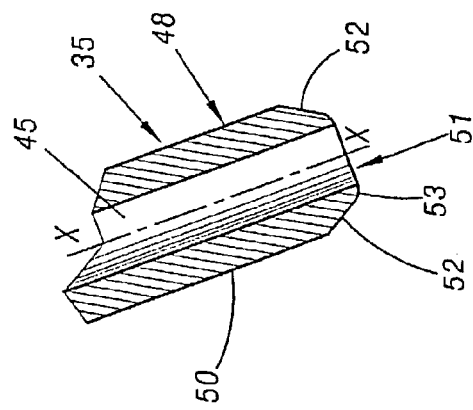
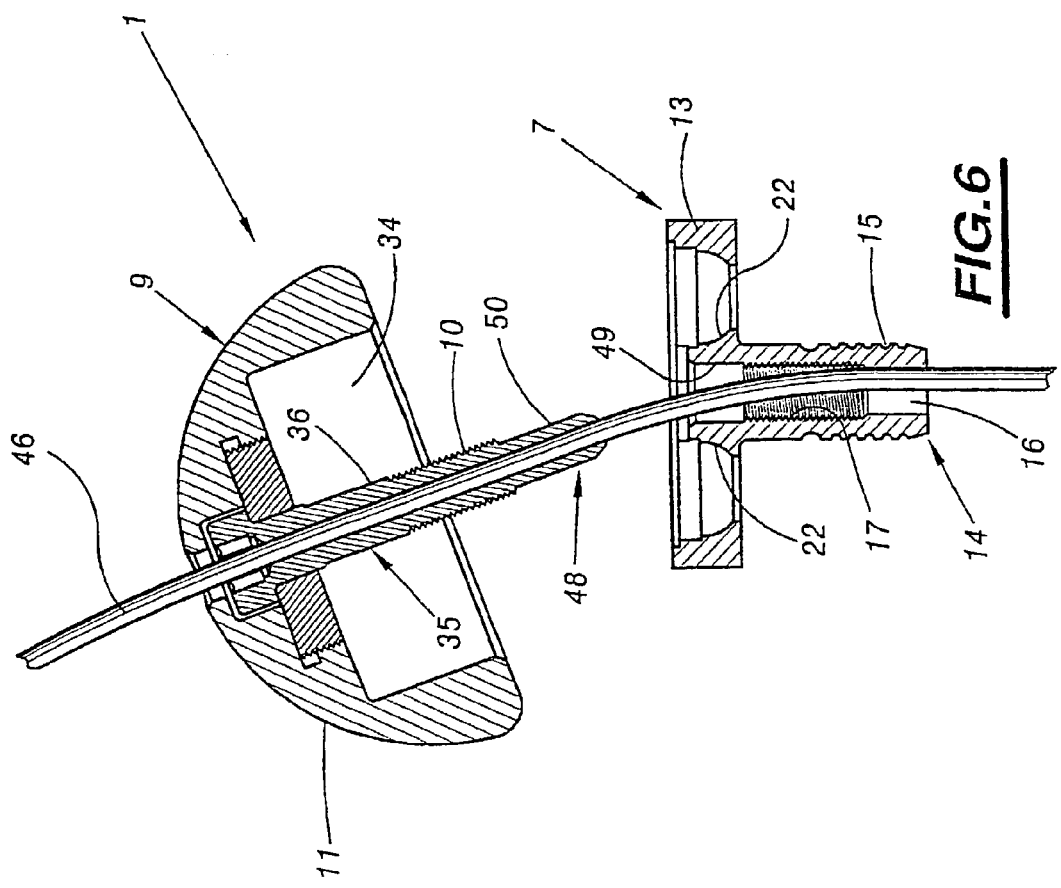

SHOULDER PROSTHESIS ASSEMBLY

BACKGROUND OF THE INVENTION

The present invention relates to a shoulder prosthesis assembly of the type comprising a metaglenoid element formed by a plate provided with a central tubular bushing together with members for anchoring in the glenoid cavity, and a glenoid sphere adapted to be fitted over the metaglenoid element. The glenoid sphere is provided with an axial screw that is free to turn relative to the glenoid sphere. This screw is adapted to be screwed into the bushing of the metaglenoid element. The glenoid sphere has a convex joint surface for co-operating with a concave cup of an associated humeral prosthesis.

The invention also provides a prosthesis forming part of the prosthesis assembly.

A prosthesis of this type is known, for example, from French patent No. 89/13366 (2 652 498) filed in the name of Medinov.

It is known that the rotator cuff is constituted by the set of shoulder muscles which comprise the deltoid, the supraspinatus, the infraspinatus, the infrascapular, and the smaller round. When massive rupture occurs of the cuff, only the deltoid remains, and that is insufficient for enabling the shoulder joint to operate properly, which requires a shoulder prosthesis to be implanted.

Prostheses are known in which the metaglenoid element is fastened to the glenoid cavity of the scapula by a plurality of screws and receives a glenoid sphere having a convex joint surface, which sphere is screwed to the periphery of the metaglenoid element.

Unfortunately, it is found that after being in use for a certain length of time, the glenoid sphere tends to become unscrewed. This causes the glenoid sphere to tilt under the metaglenoid element and destroys the threads . . . . This damage caused to the prosthesis can be sufficient to require a surgeon to remove the entire prosthesis in order to replace it.

To solve this problem, proposals were initially made to cause the facing contacting surfaces of the glenoid sphere and the metaglenoid element to be rough. That technique has turned out to be insufficient.

Proposals were then made to associate the screw of the glenoid sphere with an arrangement of complementary male and female conical bearing surfaces made respectively on the metaglenoid element and the glenoid sphere. The two conical bearing surfaces can then be moved apart or towards each other as a function of the direction in which the screw is driven in order to lock or unlock the system comprising the glenoid sphere and the metaglenoid element. A shoulder prosthesis arranged in that way is described in French patent No. 95/09395 (2 737 107) in the name of Medinov. That prosthesis gives satisfaction.

However, the heads of the screws can pass right through the metaglenoid element at the end of screw tightening if the surgeon cannot feel this end appropriately, since no special retaining means are provided. Under such circumstances, the metaglenoid element is no longer fixed to the glenoid cavity.

Another problem lies in giving the surgeon access to the metaglenoid element, which raises a difficulty with putting the glenoid sphere properly into place on the metaglenoid element. The patient is in a semi-seated position during surgery, such that the surgeon has to approach the metaglenoid element from a cantilevered-out position, with the metaglenoid element being, as it were, at the bottom of a well defined by the tissues and the muscles of the shoulder. Access to the metaglenoid element is narrow and relatively difficult, with poor visibility that makes it impossible to tell whether the glenoid sphere screw is exactly on the axis of the metaglenoid bushing.

It results that the surgeon can position the glenoid sphere incorrectly, so that the axial screw of the glenoid sphere is not exactly on the axis of the corresponding hole in the metaglenoid element. Under such circumstances, screw tightening is started when the thread on the glenoid sphere screw and the tapping in the central hole of the metaglenoid element are not properly engaged. Once the surgeon becomes aware of this faulty insertion, the threads have already become sufficiently damaged to require the entire prosthesis to be replaced. Not only must two prostheses be used, thus considerably increasing equipment cost, but the time required for the operation is doubled.

SUMMARY OF THE INVENTION

The object of the invention is to provide a glenoid prosthesis that is arranged in such a manner as to eliminate those various drawbacks.

According to the invention, the shoulder prosthesis includes means for guiding the glenoid sphere and adapted to facilitate proper placement of the screw on the metaglenoid element on the axis of the bushing.

In an embodiment of the invention, said guide means comprise a pin adapted to be capable of being slid in the tubular bushing, and the screw of the glenoid sphere presents a longitudinal axial channel opening out to both ends of the screw and allowing the pin to be inserted into said channel, such that the pin serves to guide the glenoid sphere when the screw slides along the pin until it is inserted into the tubular bushing.

Preliminary insertion of the pin in the central bushing of the metaglenoid element makes it possible to provide complete guidance of the glenoid sphere onto the axis of the central bushing of the metaglenoid element. The glenoid sphere screw can then be screwed properly into the metaglenoid bushing without any risk of damaging the threads, thereby almost completely eliminating any risk of needing to have recourse to a second prosthesis.

According to another characteristic of the invention, the members for anchoring the metaglenoid element in the glenoid cavity are screws, and means are provided to ensure that each screw comes into abutment against the metaglenoid element at the end of screw tightening.

In an embodiment of the invention, the abutment means comprise a collar formed around the head of at least one screw and projecting radially relative to a thread of the screw head, and a corresponding annular bearing shoulder arranged around the edge of a tapped hole for insertion of the screw in the metaglenoid element.

According to another possible characteristic of the invention, the abutment means comprise at least one head of a screw presenting a convex outside surface adapted to bear against a complementary concave seat formed in the wall of a hole for inserting said screw in the metaglenoid element.

These arrangements thus avoid any risk of the screw passing through the metaglenoid element at the end of screw tightening, thus guaranteeing security in the fixing of the metaglenoid element to the glenoid cavity.

BRIEF DESCRIPTION OF THE DRAWINGS

Other features and advantages of the invention appear from the following description given with reference to the accompanying drawings which show an embodiment by way of non-limiting example.

FIG. 6 is a view analogous to FIG. 5 showing the operation of engaging the glenoid sphere on the metaglenoid element by means of a guide pin.

FIG. 7 is a fragmentary axial section view on a larger scale than FIG. 5 showing the free end of the axial screw of the glenoid sphere.

DETAILED DESCRIPTION OF THE PREFERRED EMBODIMENTS

Figure 1:
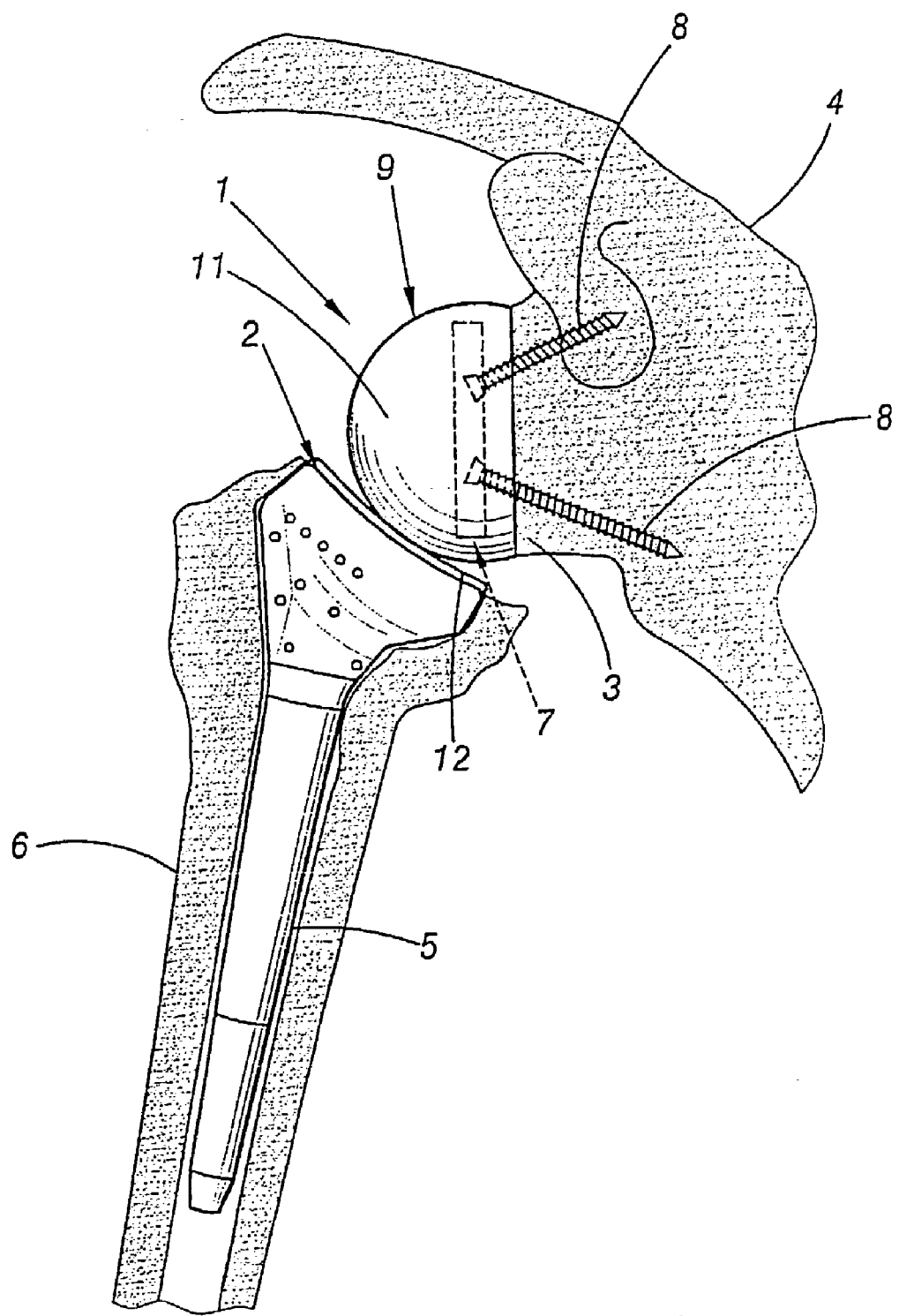
FIG. 1 is an elevation view in a front plane and on a small scale of a total shoulder prosthesis including a glenoid implant in accordance with the invention.

The total shoulder prosthesis shown in FIG. 1 comprises a glenoid implant 1 and a humeral implant 2, respectively secured to the glenoid cavity 3 of a scapula 4 and in the medullar canal 5 of a humerus 6.

The glenoid implant 1 comprises both a metaglenoid element 7 formed by a plate 13 (FIGS. 2 to 6) provided with a plurality of screws 8 for anchoring it in the glenoid cavity 3, two of which screws can be seen in FIG. 1, and also a glenoid sphere 9 adapted to be fitted over the metaglenoid element 7.

The glenoid sphere 9 presents a joint surface 11 which is convex in this embodiment, for co-operating with a complementary surface of a cup 12 of the associated humeral prosthesis 2. In this embodiment, the cup 12 has a concave surface complementary to the convex surface 11.

The plate 13 is preferably conical, being circularly symmetrical about an axis X—X and being fitted with a central bushing 14 that is preferably integrally formed with the plate 13. The central bushing 14 projects from the plate 13 and has circular ribs 15 to anchor in the bone of the metaglenoid element 7. The bushing 14 presents an axial bore 16 that has tapping 17 over a fraction of its length. The tapping 17 is extended by a bore 49 constituting a smooth zone.

Figure 3:
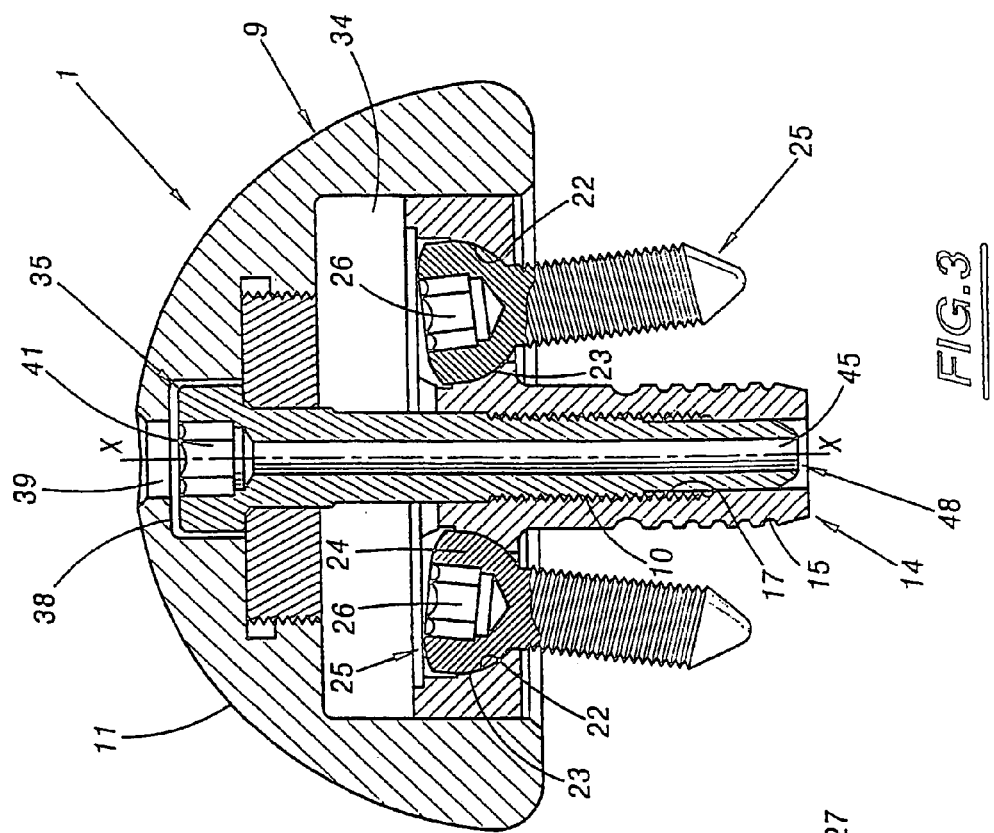
FIG. 3 is a view of the glenoid prosthesis in section on 3/3 of FIG. 4.
Figure 2:
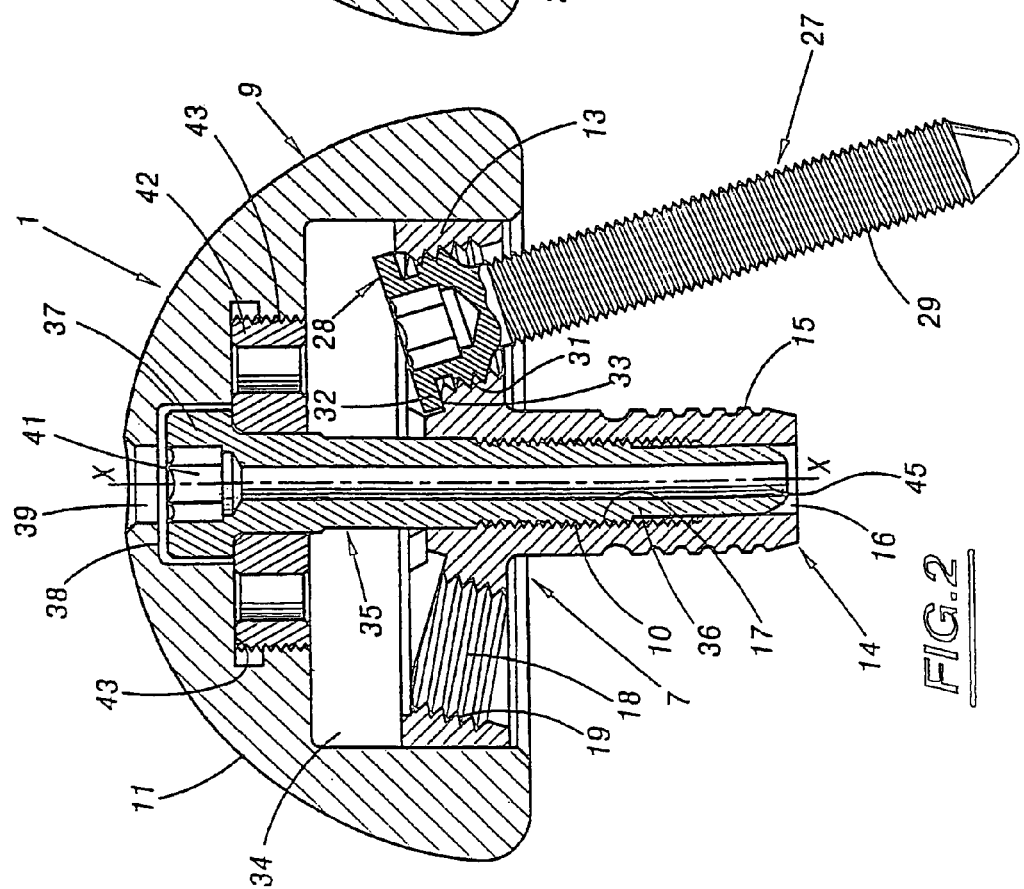
FIG. 2 is a view on a larger scale, showing the glenoid prosthesis of FIG. 1 in axial section on 2/2 of FIG. 4.
Figure 5:
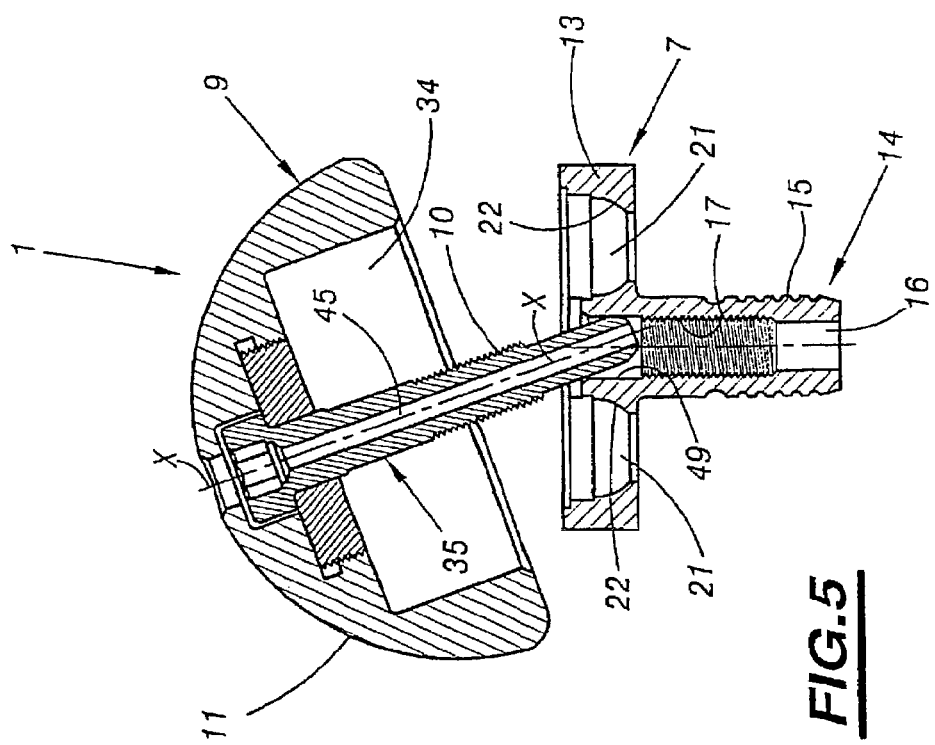
FIG. 5 is a view of the shoulder prosthesis in axial section on 3/3 of FIG. 4, showing the beginning of the operation of inserting the axial screw of the glenoid sphere into the central bushing of the metaglenoid element.
Figure 4:
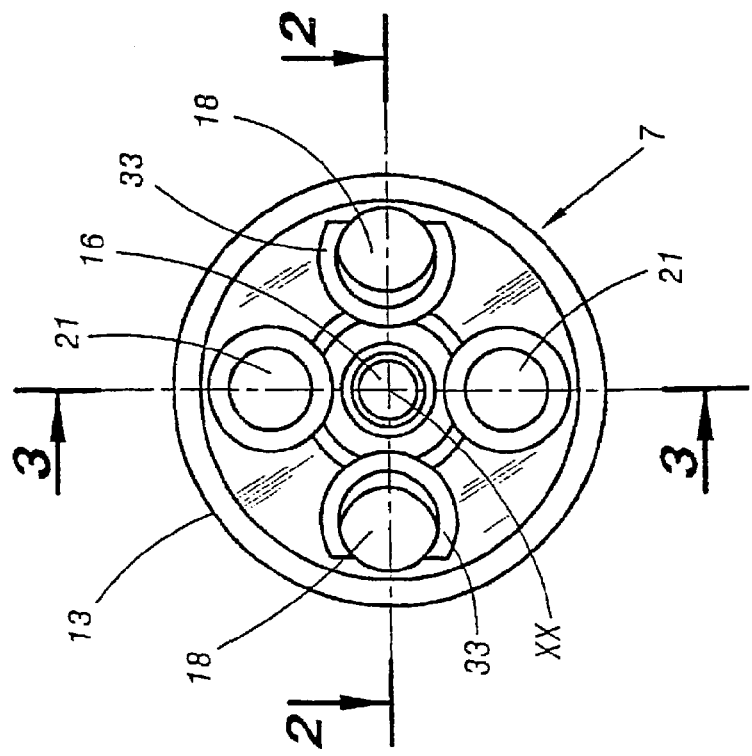
FIG. 4 is a plan view of the metaglenoid element of the shoulder prosthesis of FIGS. 1 to 3.

The plate 13 is pierced by four holes for passing the glenoid anchor screws of the metaglenoid element 7. Two of these holes 18 are diametrically opposite and present tapping 19. Their axes diverge symmetrically about the axis X—X. The other two holes 21 are diametrically opposite and are offset from the holes 18 by angular intervals that are preferably equal to 90°. The non-tapped holes 21 are defined by walls 22 constituting concave bearing seats for complementary convex surfaces 23 defining the heads 24 of the bone-anchor screws 25 for anchoring the metaglenoid element 7 in the glenoid cavity 3 (FIG. 3).

The seats 22 are oriented in such a manner that once the screws 25 have been put into place thereon they are disposed so as to diverge relative to the central bushing 14 and symmetrically thereabout. Sockets 26, e.g. hexagonal sockets, are formed in the heads 24 to enable the screws 25 to be tightened by means of a corresponding tool (not shown).

The holes 18 can receive diverging screws 27 each constituted by a head 28 and a threaded shank 29. The head 28 has a thread 31 suitable for screwing into the tapping 19, and an end collar 32 formed around the head 28. The collar 32 projects radially relative to the tapping 31 and can be brought to bear against a corresponding angular shoulder 33 arranged around the edge of the hole 18 in which the screw 27 is inserted.

The collar 32 constitutes abutment means for the screw 27 in the glenoid cavity 3 at the end of screw tightening, preventing the screw 27 from being moved in further as soon as the collar 32 comes into abutment on the associated shoulder 33. Similarly, the concave seats 22 act relative to the associated screws 25 as abutments for stopping them in the metaglenoid element 7 once they have been screwed into the glenoid cavity 3, as soon as the screws 25 have been engaged far enough for the surfaces 23 of the heads 24 to come into contact with the seats 22.

This arrangement prevents the screws 25 and 27 from passing through the metaglenoid element 7 at the end of screw tightening.

The glenoid sphere 9 is made of a substantially hemispherical part whose spherical surface 11 is complementary to the corresponding joint surface of the cup 12. The glenoid sphere 9 has arranged therein a conical recess 34 that is circularly symmetrical about the axis X—X, and that is dimensioned in such a manner as to enable the plate 13 to be inserted therein. The glenoid sphere, which is circularly symmetrical about the axis X—X, is then fitted over the metaglenoid element 7.

The glenoid sphere 9 is provided with an axial screw 35 that is free to rotate relative to the glenoid sphere 9. The shank 36 of the screw 35 presents a thread 10 over a fraction of its length and it can be screwed into the tapping 17 of the bushing 14. The screw 35 has a head 37 suitable for being inserted in a housing 38 that is circularly symmetrical about the axis X—X and that opens out into the polar cap of the surface 11 via an axial orifice 39. This orifice allows the end of a tool for tightening the screw 35 to be inserted, which tool can be received in a socket 41 of complementary shape.

After the head 37 has been inserted in the housing 38, the screw 35 is held in place by a threaded washer 42 placed in a tapped housing 43 that is coaxial with the housing 38 about the axis X—X.

A longitudinal axial channel 45 is arranged in the screw 35 opening out at both ends of the screw, i.e. at one end in the socket 41 and in the orifice 39. The prosthesis assembly also comprises means for guiding the glenoid sphere 9, and adapted to make it easier to install on the metaglenoid element 7. In the embodiment shown, these guide means comprise a pin 46 that preferably presents some flexibility, being adapted to be slid initially into the axial bore 16 of the bushing 14 and secondly through the longitudinal channel 45 of the screw 35 (FIG. 6). The pin 46 is preferably made of metal, and its diameter is advantageously slightly smaller than the diameter of the channel 45 in the screws 35.

The screw 35 has a smooth free end 48 whose tip is chamfered so as to facilitate insertion into the inlet of the tubular bushing 14. The guide means for the screw 35 further comprise the bore constituting a smooth zone 49 arranged in the inlet of the bushing 14 and followed by the tapping 17. The chamfered tip 51 preferably has an annular surface 52 whose longitudinal section is rectilinear (i.e. a conical surface) and which is followed to the free end of the tip 51 by a rounded annular surface 53, preferably constituted by a spherical fillet. At its end remote therefrom, the conical section 52 joins a smooth zone 50 followed by the thread 10.

The pin 46 is used by the surgeon as follows.

The metaglenoid element 7 is initially anchored in the glenoid cavity 3 by impacting the bushing 14 and by tightening the screws 25, 27. Thereafter, the surgeon inserts one end of the pin 46 in the bore 16 of the bushing 14. Using a screwdriver that has a cannula, the surgeon then presents the glenoid sphere 9 to the inlet of the well formed in the tissues and the muscles of the shoulder, with the bottom of the well being constituted by the metaglenoid element 7, the end of the pin 46 being threaded into the axial channel 45. The surgeon then causes the glenoid sphere 9 to slide along the pin 46 until the free end 48 of the screw 35 engages in the bore constituting a smooth zone 49 (FIG. 6). The chamfered and rounded tip 51 makes it easier to insert the screw 35 into the bushing 14 without damaging the tapping 17 because of the bore constituting a smooth zone 49, and without damaging the thread 10 because of the smooth zone 50. As soon as the screw 35 is properly on the axis X—X of the bushing 14, the surgeon tightens the screw 35 until the glenoid sphere 9 becomes impacted on the metaglenoid element 7 (FIGS. 3 and 4) and then withdraws the screwdriver and the pin.

The arrangement of the rounded fillet 53 of the conical zone 52, of the smooth zone 50, and of the bore constituting a smooth zone 49 of the bushing 14 can be arranged to provide proper guidance for the screw 35 in the bushing 14, either in combination with a guide pin 46 (FIGS. 5 and 6) or without one. Under such circumstances, the screw 35 can have the axial channel 45 or it can be solid. Nevertheless, the combination of the bore 16, the pin 46, the end 48 with its smooth zone 50, and the bore constituting a smooth zone 49 of the bushing 14 provides the most satisfactory guidance for the glenoid sphere 9 up to its proper position on the axis X—X of the metaglenoid element 7.

In other words, the following variants are possible:

the screw 35 can have a cannula, i.e. can present the axial channel 45 and can be used together with the guide pin 46 without any offset between the thread of the screw 35 and the tapping of the bushing 14: under such circumstances, the thread 10 extends almost to the free end of the screw 35, and the bore constituting a smooth zone 49 is replaced by additional tapping 17;

the screw 35 does not have a cannula, and therefore does not present an axial channel 45, but the thread 10 and the tapping 17 are offset as shown in the drawings, i.e. a smooth zone 50 is provided on the screw 35 and a bore constituting a smooth zone 49 is arranged in the bushing 14; and the screw 35 has a cannula and in addition the thread 10 and the tapping 17 are offset, i.e. the smooth zone 50 and the tip 51 are arranged on the end 48 of the screw, while a bore constituting a smooth zone 49 is arranged in the inlet of the channel 16 in the bushing 14.

The end 48 of the screw 35 can have a different profile, for example it could have a simple conical chamfer such as 52, or it could have no more than a rounded end fillet of appropriate size.

The indications for the above-described glenoid prosthesis 1 are essentially as follows: traumatisms, arthrosis between the humerus and the scapula, rheumatoid polyarthritis. In general, the shoulder prosthesis of the invention is indicated for pathologies of the rotator cuff.

What is claimed is:

1. A shoulder prosthesis assembly, comprising:
a metaglenoid element comprising a plate that includes a central tubular adapter having an axial bore that is threaded over a fraction of a length of said axial bore, said tubular adapter coacts with at least one anchoring member to anchor said metaglenoid element in a glenoid cavity; and
a glenoid sphere adapted to be fitted over said metaglenoid element and having an axial screw that is capable of being screwed into said tubular adapter, said glenoid sphere having a joint surface for co-operating with a cup of an associated humeral prosthesis,
wherein said axial screw includes cylindrical means for guiding said glenoid sphere with respect to said metaglenoid element, said means for guiding cooperates with a smooth cylindrical zone arranged in an inlet of said axial bore of said tubular adapter and allows axial insertion of said axial screw into said axial bore of said tubular adapter without damaging threads of said axial bore.

2. The prosthesis assembly according to claim 1, wherein said means for guiding comprise a pin slidable in said tubular adapter, and wherein said axial screw includes a longitudinal axial channel open at both ends of said axial screw and allowing the pin to be inserted into said axial channel, such that the pin serves to guide the glenoid sphere as the axial screw slides along the pin when the axial screw is inserted into the tubular adapter.

3. The prosthesis assembly according to claim 2, wherein said axial channel opens at one of said ends into a socket arranged in a head of the axial screw and that is suitable for co-operating with a screwdriving tool.

4. The prosthesis according to claim 2, wherein said means for guiding comprise a smooth free end of the axial screw and said smooth zone arranged in said inlet of the axial bore and wherein the fraction of the axial bore that is threaded is downstream from said smooth zone in a direction of insertion of said axial screw into said axial bore.

5. The prosthesis assembly according to claim 1, wherein said means for guiding comprise a smooth free end of the axial screw, and said smooth zone in said inlet of said axial bore is adjacent a threaded zone.

6. The prosthesis assembly according to claim 5, wherein said smooth free end has a chamfered tip defining a conical annular surface and a rounded annular surface.

7. The prosthesis assembly according to claim 1, wherein said at least one anchoring member are first and second screws that abut against abutment elements of said metaglenoid element when said first and second screws are tightened.

8. The prosthesis assembly according to claim 7, wherein said abutment elements comprise a collar formed around a head of one of said first and second screws and projecting radially relative to a thread of the respective screw head, and a corresponding annular bearing shoulder arranged around an edge of a threaded hole for insertion of said one of said first and second screws in the metaglenoid element.

9. The prosthesis assembly according to claim 7, wherein the abutment elements comprise a concave seat formed in a wall of a hole for inserting one of said first and second screws in the metaglenoid element, and wherein a head of said one of said first and second screws presenting a convex outside surface adapted to bear against said concave seat.

10. A shoulder prosthesis assembly, comprising:
a metaglenoid element comprising a plate having a central tubular adapter extending from said plate, said tubular adapter including a central axial bore having non-threaded first and second sections with a threaded section between said non-threaded first and second sections; and a glenoid sphere fitted onto said metaglenoid element and having an axial screw that screws into said tubular adapter, said glenoid sphere having a joint surface for co-operating with a cup of an associated humeral prosthesis, wherein said axial screw includes a smooth cylindrical surface that contacts said nonthreaded first section when said glenoid sphere is inserted into said metaglenoid element.

11. The prosthesis assembly according to claim 10, further comprising a pin slidable into said tubular adapter, and wherein said axial screw includes a longitudinal axial channel that allows the pin to be inserted into said axial channel, such that the pin serves to guide the glenoid sphere as the axial screw slides along the pin when the axial screw is inserted into the tubular adapter.

* * * * *